(12) United States Patent
Norman et al.

(10) Patent No.: US 8,272,857 B2
(45) Date of Patent: Sep. 25, 2012

(54) METHOD AND SYSTEM FOR LOADING OF TUBING INTO A PUMPING DEVICE

(75) Inventors: Gerould W. Norman, Jacksonville, FL (US); Craig L. Drager, Jacksonville, FL (US); Michael L. Koltz, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 993 days.

(21) Appl. No.: 12/036,148

(22) Filed: Feb. 22, 2008

(65) Prior Publication Data

US 2009/0214365 A1    Aug. 27, 2009

(51) Int. Cl.
*F04B 43/12* (2006.01)
*F04B 45/06* (2006.01)

(52) U.S. Cl. ....... 417/474; 417/53; 417/476; 417/477.1; 417/477.2; 417/477.3; 417/477.8; 417/477.9; 417/477.12; 604/153; 604/154

(58) Field of Classification Search ............ 417/53, 417/474, 476, 477.1, 477.2, 477.3, 477.8, 417/477.9, 477.12, 477.14; 604/153, 154
See application file for complete search history.

(56) References Cited

U.S. PATENT DOCUMENTS

| | | | |
|---|---|---|---|
| 3,402,673 A * | 9/1968 | Ballentine et al. ......... 417/477.1 |
| 4,187,057 A | 2/1980 | Xanthopoulos | |
| 4,537,561 A | 8/1985 | Xanthopoulos | |
| 4,545,744 A * | 10/1985 | Weber et al. ............... 417/475 |
| 4,599,055 A * | 7/1986 | Dykstra .................... 417/477.2 |
| 4,798,580 A | 1/1989 | DeMeo et al. | |
| 4,824,339 A | 4/1989 | Bainbridge et al. | |
| 4,861,242 A | 8/1989 | Finsterwald | |
| 4,925,376 A | 5/1990 | Kahler | |
| 5,133,650 A | 7/1992 | Sunderland et al. | |
| 5,190,448 A | 3/1993 | Lane et al. | |
| 5,249,937 A | 10/1993 | Aubert | |
| 5,257,917 A | 11/1993 | Minarik et al. | |
| 5,387,088 A | 2/1995 | Knapp et al. | |
| 5,433,588 A | 7/1995 | Monk et al. | |
| 5,447,417 A * | 9/1995 | Kuhl et al. ............... 417/477.11 |
| 5,460,490 A | 10/1995 | Carr et al. | |
| 5,620,312 A | 4/1997 | Hyman et al. | |
| 5,792,167 A | 8/1998 | Kablik et al. | |
| 5,927,956 A * | 7/1999 | Lim et al. ................. 417/477.13 |
| 5,928,257 A | 7/1999 | Kablik et al. | |

(Continued)

OTHER PUBLICATIONS

Watson-Marlow Pumps. "300 Series OEM Systems," http://www.watson-marlow.com/watson-marlow/p-oem300.htm, printed Sep. 23, 2011. (14 pages; includes product data for Watson 313 and 314 Pump cited in the IDS of Feb. 22, 2008 in U.S. Appl. No. 12/036,148.).*

(Continued)

*Primary Examiner* — Charles Freay
*Assistant Examiner* — Christopher Bobish
(74) *Attorney, Agent, or Firm* — Dicke, Billig & Czaja PLLC

(57) ABSTRACT

A tube-positioning system for loading tubing into a peristaltic pump includes a holder and a first tube segment. The holder includes a shell configured to slidably fit onto an exterior of a pump and a pair of guides extending upward from opposite side walls of the shell. The first tube segment has a fixed length and extends between the pair of guides with each end of the first tube segment secured within one of the respective guides.

24 Claims, 7 Drawing Sheets

U.S. PATENT DOCUMENTS

| | | | |
|---|---|---|---|
| 6,007,556 | A | 12/1999 | Kablik et al. |
| 6,090,123 | A | 7/2000 | Culp et al. |
| 6,171,300 | B1 | 1/2001 | Adams |
| 6,342,061 | B1 | 1/2002 | Kauker et al. |
| 6,406,267 | B1 * | 6/2002 | Mondiere ............ 417/53 |
| 6,652,488 | B1 | 11/2003 | Keast et al. |
| 6,731,216 | B2 | 5/2004 | Ho et al. |
| D513,801 | S | 1/2006 | Stubkjaer |
| 7,018,182 | B2 * | 3/2006 | O'Mahony et al. ........ 417/476 |
| 7,273,359 | B2 * | 9/2007 | Blight et al. .......... 417/477.13 |
| 2005/0047925 | A1 * | 3/2005 | Davis ................ 417/53 |
| 2005/0069436 | A1 * | 3/2005 | Shibasaki ............. 417/476 |
| 2005/0069437 | A1 * | 3/2005 | Mittelstein et al. ........ 417/477.2 |
| 2007/0258838 | A1 * | 11/2007 | Drake et al. .......... 417/477.11 |
| 2007/0296744 | A1 * | 12/2007 | Kubota et al. ............. 347/7 |
| 2008/0114312 | A1 * | 5/2008 | Muri et al. ............. 604/294 |

OTHER PUBLICATIONS

Watson Marlow Pumps, "313 and 314 OEM pumpheads," http://www.watson-marlow.com/watson-marlow/pop313oem.html, printed Nov. 14, 2007. (3 pages).

* cited by examiner

METHOD AND SYSTEM FOR LOADING OF TUBING INTO A PUMPING DEVICE

BACKGROUND

The present disclosure relates to fluid delivery systems. In particular, it relates to fluid delivery systems for medical appliances.

Certain surgical appliances use a supply of fluid for irrigation of a surgical site on a patient as well as for cooling of the surgical appliance. Some non-limiting examples of this type of surgical appliance include micro-debriders, otologic drills, and the like. One common method of providing consistent fluid delivery to a surgical appliance includes pumping fluid through medical tubing via a positive displacement pump, such as a peristaltic pump. Peristaltic pumps are desirable for many reasons, such as their ability to maintain sterility of the fluid and cleanliness of the pump because the fluid flows through the medical tubing and does not come into contact with components of the pump. For these reasons, a peristaltic pump also can be used for delivering medications via an intravenous delivery system and/or for other medical applications. In each case, some type of tubing is placed within the peristaltic pump to allow its rollers to cyclically engage the tubing to provide the desired pumping action.

Despite the many advantages of peristaltic pumps for use in medical applications, there are some drawbacks. For example, proper placement of tubing within the pump continues to remain a challenge. In some conventional pumps, an operator uses their hands to feed a segment of the tubing into position within the pump. Despite the best intentions of the operator, the tubing is frequently not aligned properly within the pump, resulting in inconsistent fluid flow and/or the pumping of an insufficient volume of fluid with each cycle of the peristaltic pump. This difficulty arises, in part, from the awkwardness of using two hands to align and place the tubing relative to one or more rollers of the peristaltic pump. At the same time, a user attempts to maintain a proper angle of the tubing as it extends through the pump. A further challenge arises as an operator attempts to close the door of the pump while still maintaining the proper tube positioning. To make matters worse, misunderstandings are common among operators in the field as to what actually constitutes proper tube positioning and as to what is included in the proper technique.

Accordingly, conventional fluid delivery systems are sometimes operated without properly installed tubing, thereby diminishing the other well-established advantages of using peristaltic pumps for supplying fluids to medical appliances.

DETAILED DESCRIPTION

Embodiments of the present disclosure are directed to insuring consistent fluid flow through tubing to a medical appliance. In particular, these embodiments provide for proper positioning of medical tubing within a peristaltic pump, thereby allowing the proper volume of fluid to be moved through the tubing by the pump. To this end, a holder is provided for holding one or more segments of tubing in a predetermined configuration so that upon slidably fitting the holder onto a pump assembly, the segments of tubing are properly loaded relative to the interior components (e.g., rollers) of the pump. The holder allows for one-handed loading of the tubing. In some embodiments, the holder includes a pair of guides to insure that the tubing extends within, and out of the, pump assembly at the proper angle. In some embodiments, the tubing includes a fixed length of tubing that extends between the guides of the holder to insure that the segment of tubing that is engaged within the pump assembly avoids unwanted stretching and maintains a generally constant length. This arrangement helps the tubing to properly open and close during the cyclic rotation of the rollers of the pump.

In general terms, embodiments of the present disclosure can be used to provide controlled fluid delivery to any medical appliance receiving fluids via medical tubing via the action of a peristaltic pump. Accordingly, embodiments of the invention are not limited solely to use with surgical appliances, but can be employed with a wide variety of medical appliances.

These and other embodiments are described more fully in association with FIGS. 1-15.

Figure 1:
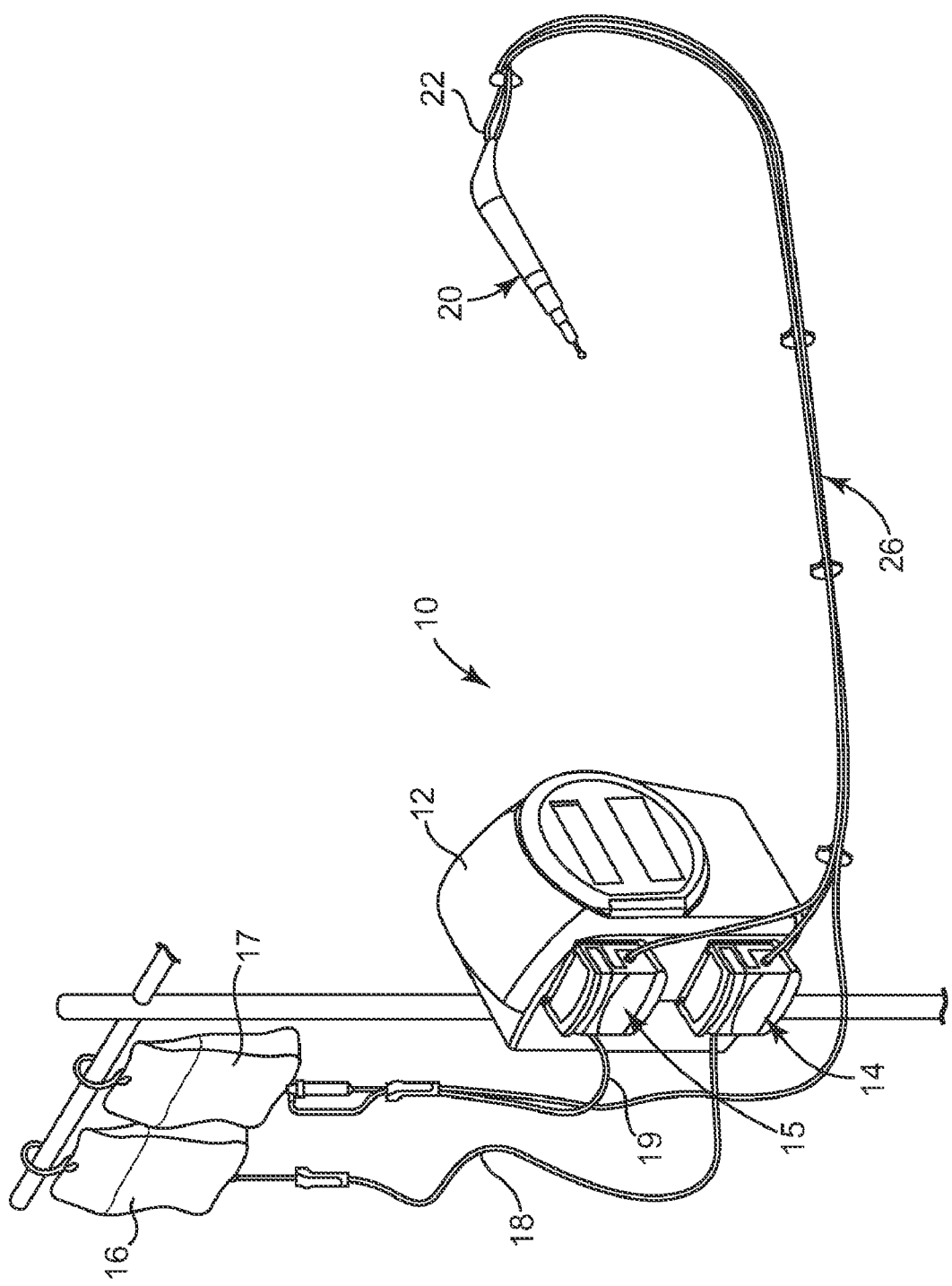
FIG. 1 is perspective view of a system for delivering fluid to a medical appliance, in accordance with principles of the present disclosure.

A fluid delivery system 10 in accordance with aspects of the present disclosure for supplying fluid to a medical appliance is shown in FIG. 1. The system 10 includes a fluid manager 12 (e.g., a console), pump assemblies 14, 15 and a medical appliance 20. Fluid stored in fluid containers 16 and 17 is supplied via the respective tubes 18, 19 to pump assemblies 14, 15 for pumping to medical appliance 20 as controlled by fluid manager 12. In one aspect, tubes 18, 19 form a part of a tubing array 26 that extends to and is fluidly connected to a proximal end 22 of medical appliance 20. The pump assemblies 14, 15 are mounted onto the fluid manager 12 and in some embodiments, are releasably secured relative to the fluid manager 12 to allow convenient replacement of one or more of the pump assemblies 14, 15.

Figure 2:
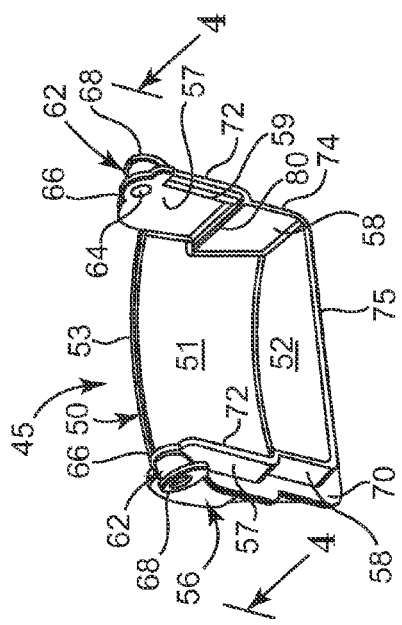
FIG. 2 is a perspective view of a front portion of a holder, in accordance with principles of the present disclosure.
Figure 3:
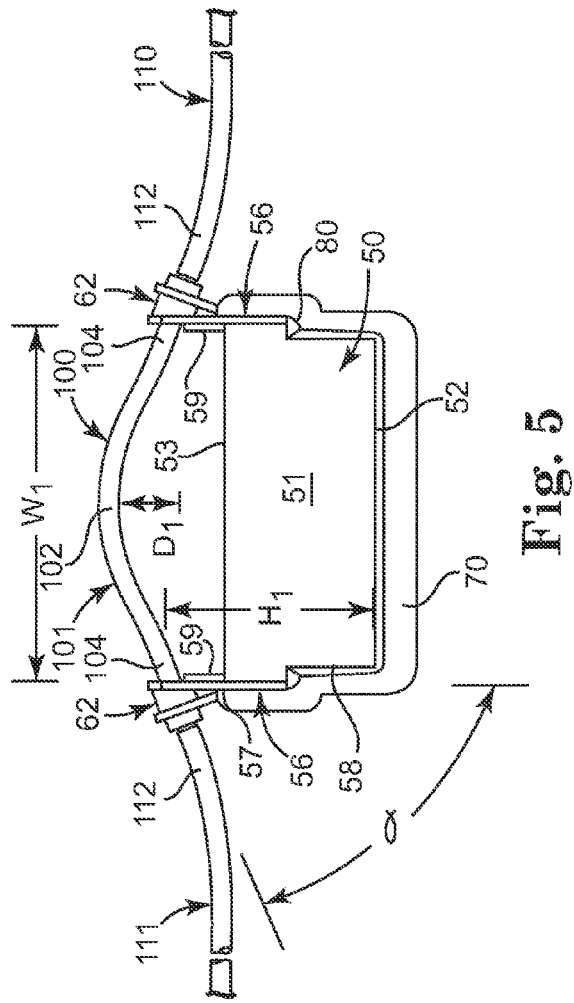
FIG. 3 is a perspective view of a back portion of the holder of FIG. 2.

With the above general construction of system 10 in mind, a holder 45 for loading tubing into a pump assembly (e.g., pump assemblies 14 and 15) is shown in FIGS. 2-3. In general terms, the holder 45 can assume a variety of forms and is sized and shaped to slidably fit over and remain engaged with one of the pump assemblies 14 or 15 (FIG. 1) to position a segment of tubing for engagement with interior components of the respective pump assemblies 14, 15. In general terms, holder 45 comprises a shell 50 forming a recess or pocket that is sized and shaped to slidably fit over and securely engage an exterior housing of a pump assembly, such as pump assembly 150 as later described in association with FIGS. 8-9. In one embodiment, the shell 50 of holder 45 is defined by a front wall 51, a bottom wall 52, a top edge 53, and side walls 56. In addition, in some embodiments, a flange 70 extends outwardly from the bottom wall 52 and the side walls 56 of the shell 50. In another aspect, the side walls 56 include a rear edge 72 and the bottom wall 52 includes a rear edge 75. In some embodiments, each side wall 56 of shell 50 includes an upper portion 57 and a lower portion 58 with upper portion 57 extending vertically upward relative to the top edge 53 of pocket 50.

In some embodiments, each side wall 56 of shell 50 also includes a shoulder 80 interposed between the upper portion 57 and the lower portion 58, which results in the lower portion 58 being narrower than the upper portion 57. In one aspect, the shoulder 80 and the lower portion 58 together facilitate grasping of the holder 45 between a thumb and fingers of an operator in an "opposed gripping" maneuver, which in turn, facilitates one-handed mounting of the holder 45 (and tubing) onto one of the pump assemblies 14, 15. This one-handed mounting maneuver is illustrated later in association with FIG. 9.

Figure 5:
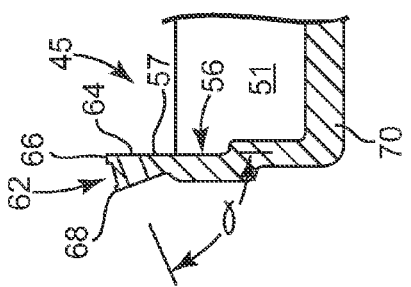
FIG. 5 is a front plan view of a segment of tubing mounted relative to a holder, in accordance with principles of the present disclosure.

In some embodiments, the upper portion 57 of each side wall 56 (of holder 45) includes a vertical rib 59 protruding from an inner surface of upper portion 57, as illustrated in FIGS. 2-3 and 5. These vertical ribs 59 are configured to releasably engage a corresponding feature of a pump assembly (e.g., pump assembly 14, 15) such as a slot or protrusion, sized and shaped to releasably engage the vertical ribs 59 of holder 45. With this arrangement, when the holder 45 is slidably mounted onto a housing of a pump assembly (see FIG. 9), the vertical ribs 59 enable snap-fitting of the holder 45 onto the housing of the pump assembly. Accordingly, this snap-fitting feature stabilizes a position of holder 45 during and after loading tubing within pump assembly, which is further described later in association with FIGS. 8-13.

Figure 4:
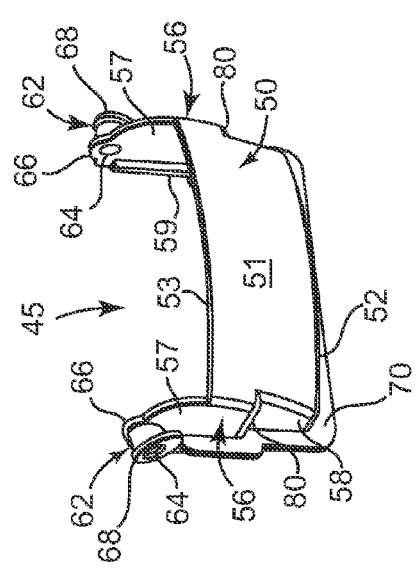
FIG. 4 is a cross-sectional view of FIG. 3 as taken along line 4-4.

As shown in FIGS. 2-4, in some embodiments, holder 45 further comprises a pair of guides 62 extending outwardly from the upper portion 57 of the respective side walls 56 of shell 50. Each guide 62 defines a hollow elongate sleeve 64 extending between an inner end 66 and an outer end 68. In some embodiments, each of the inner end 66 and the outer end 68 form a flange.

As shown in FIGS. 4-5, in some embodiments, the elongate sleeve 64 defined by each guide 62 forms an acute angle ($\alpha$) relative to the respective side walls 56 of holder 45 wherein the angle $\alpha$ falls within a range of 60 to 80 degrees. In some embodiments, the angle ($\alpha$) is about 70 degrees. In combination, a height of side wall 56 (illustrated in FIG. 5 as H1) and the angle ($\alpha$) of the sleeve 64 are selected to cause any tubing extending through the guide 62 to extend vertically upwardly at an angle for entry within a roller-tube engagement zone 185 of a pump assembly (e.g., pump assembly 14, 15), as later shown in more detail in FIGS. 10 and 12. In one aspect, a longitudinal axis of each one of the respective sleeves 64 (of the respective guides 62) is oriented toward convergence upon each other adjacent the roller-tube engagement zone 185 of the pump assembly, as later shown in FIGS. 10 and 12.

Figure 6:
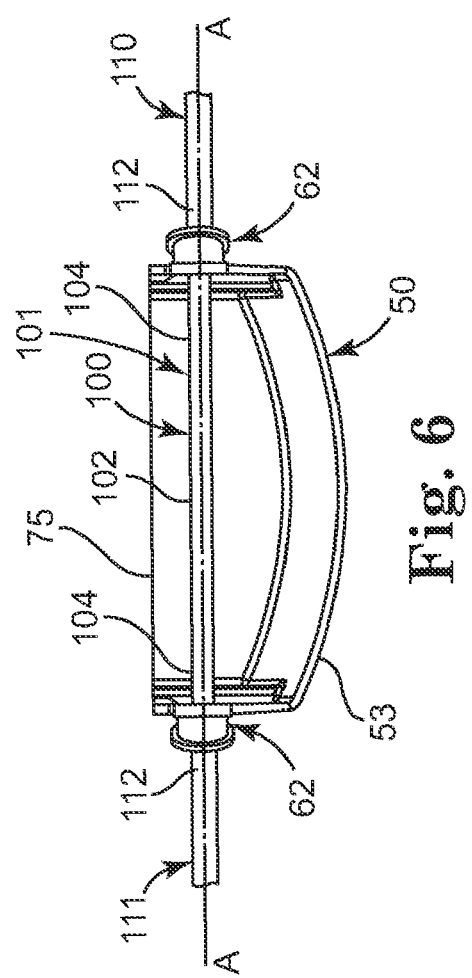
FIG. 6 is a top view of the holder and segment of tubing of FIG. 5.

As further illustrated in FIGS. 5-6, in some embodiments, a tubing array 100 supported by guides 62 of holder 45 includes first tube segment 101, second tube segment 110, and third tube segment 111, as illustrated in FIGS. 5-6. In one aspect, first tube segment 101 is interposed between, and is in fluid communication with, second tube segment 110 and third tube segment 111. In another aspect, first tube segment 101 extends between guides 62 of holder 45 while second tube segment 110 and third tube segment 111 extend laterally outward from guides 62 (and from side walls 56) of holder 45.

In some embodiments, first tube segment 101 comprises a separate and independent portion of tubing and is joined to second tube segment 110 and third tube segment 111 via a connector 130, as later described and illustrated in association with FIGS. 7A-7B.

Referring again to FIGS. 5-6, first tube segment 101 includes a pair of opposite ends 104 and a midportion 102 while each of the respective second and third tube segments 110, 111 includes an inner end 112. In one aspect, first tube segment 101 has a length selected to be greater than a width (represented by W1 in FIG. 5) between guides 62, so that with first tube segment 101 mounted relative to guides 62, midportion 102 of first tube segment 101 extends above guides 62 by a distance D1. In one aspect, the distance D1 is selected so that when holder 45 is used to load midportion 102 of first tube segment 101 will be positioned above an uppermost roller 182 of pump assembly 150, as described later in more detail in association with FIGS. 10-12. In another aspect, the combination of the angled position of guides 62 and the selected fixed length of first tube segment 101 causes midportion 102 of first tube segment 101 to form an arcuate shape within the roller-tube engagement zone 185.

In one aspect, as illustrated in FIG. 5, guides 62 are laterally spaced apart by a width (W1) that is substantially the same as a width (illustrated as W2 in FIG. 8) of an exterior housing of a pump assembly 150. This arrangement contributes to the slidable engagement of holder 45 relative to the pump assembly 150. This arrangement also causes the ends 104 of first tube segment 101 to be positioned within the tube-gripping mechanisms 170 of pump assembly 150, as later described in association with FIGS. 10-12.

In one embodiment, all three of the respective tube segments 101, 110, and 111 are made from the same material. In another embodiment, the first tube segment 101 is made from a material different than the material of the second tube segment 110 and third tube segment 111. For example, in one embodiment, the first tube segment 101 is made from a silicone material while the second and third tube segments 110, 111 are made from a polyvinyl chloride (PVC) material.

Figure 7A:
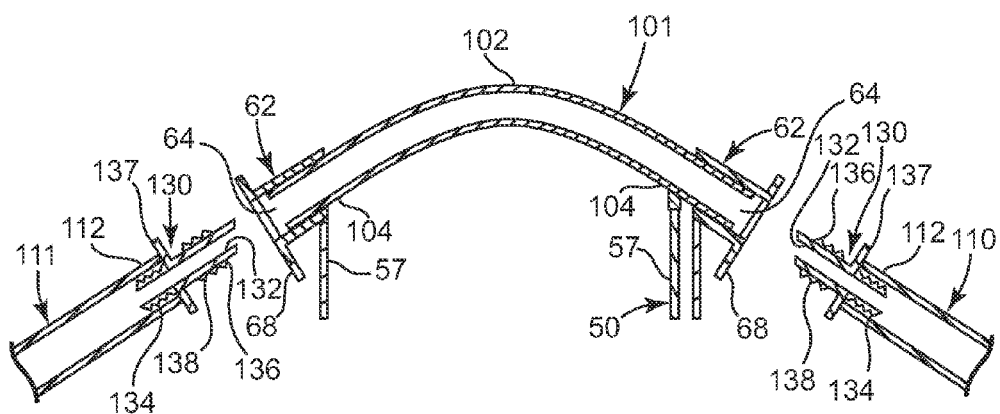
FIG. 7A is a cross-sectional view illustrating a method of installing a segment of tubing into the holder of FIGS. 1-6, in accordance with principles of the present disclosure.
Figure 7B:
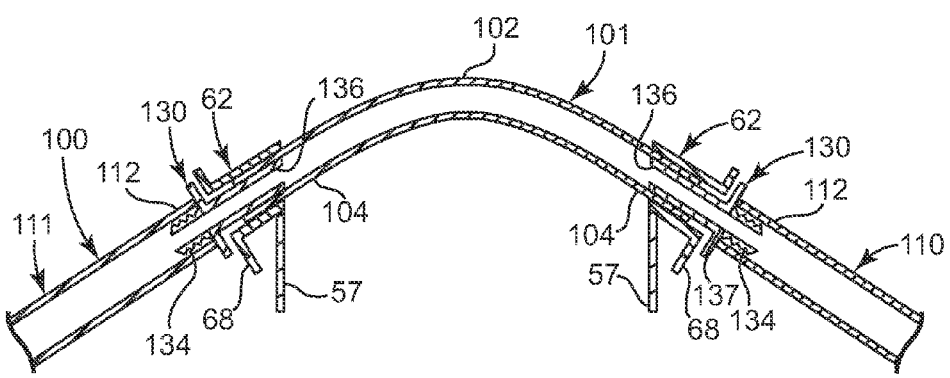
FIG. 7B is a cross-sectional view illustrating a method of installing a segment of tubing into the holder of FIGS. 1-6, in accordance with principles of the present disclosure.

FIGS. 7A-7B further illustrate the relationship of the respective tube segments 101, 110, 111 relative to each other and relative to guides 62 of holder 45. In most instances, an operator in the field would expect to receive the tubing array 100 and the holder 45 already assembled together as a "ready-to-use" package not requiring assembly. However, to highlight principles of the present disclosure, various aspects of the interconnection of the respective tube segments 101, 110, and 111 relative to each other and relative to holder 45 will be described.

Accordingly, in some embodiments, each end 104 of first tube segment 101 is slidably inserted into, and frictionally engages, the sleeve 64 of one of the respective guides 62 to secure the first tube segment 101 relative to the guides 62 of holder 45, as illustrated in FIG. 7A.

In addition, prior to installation relative to guides 62 of holder 45, the ends 112 of second tube segment 110 and of third tube segment 111 are adapted by mounting a connector 130 thereto. In general terms, connector 130 provides a mechanism to establish a mechanical connection that links the second and third tube segments 110,111 relative to first tube segment 101 while also anchoring the respective tube segments 101, 110, 111 relative to guides 62. At the same time, connector 130 establishes and maintains a fluid communication pathway between the respective tube segments 101, 110, 111. Accordingly, connector 130 secures the respective tube segments 101, 110, 111 relative to each other and relative to holder 45, thereby enabling holder 45 to act as a tool for loading the tubing array 100 relative to the pump assembly 150.

While connector 130 can take many forms, in some embodiments, connector 130 defines a conduit 132 extending between a first end 134 and a second end 136, as shown in FIG. 7A. In one aspect, connector 130 includes a flange 137 interposed between the first end 134 and second end 136. In another aspect, each of the first end 134 and second end 136 include a barbed outer surface 138 (including one or more barbs) for frictionally engaging an inner wall of an end 112 of one of the respective tube segments 110, 111 or an end 104 of first tube segment 101. Accordingly, with this general construction in mind, the end 112 of each one of the respective tube segments 110, 111 is slidably mounted onto a first end 134 of one of the respective connectors 130 until the end 112 abuts the flange 137 of each respective connector 130, as illustrated in FIG. 7A.

With the respective tube segments 110, 111 already attached to the first end 134 of connector 130, the second end 136 of connector 130 is slidably inserted into and through sleeve 64 of guide 62 until second end 136 of connector 130 slides within and frictionally engages end 104 of first tube segment 101 that is already mounted relative to guide 62, as illustrated in FIG. 7B. In this manner, all three tube segments 101, 110, and 111 are secured together via connector 130 while simultaneously being secured relative to guides 62 of holder 45.

In accordance with principles of the present disclosure, this arrangement provides and maintains a fixed length of tubing (e.g., first tube segment 101) between guides 62 to minimize unwanted slippage of tubing through the pump assembly during pumping, as sometimes occurs with conventional tubing and pump arrangements. Moreover, the arrangement illustrated in FIG. 7B insures that ends 104 of first tube segment 101 extend at the proper angle to position the ends 104 for proper engagement by a tube-gripping mechanism 170 of pump assembly 150, as described later in more detail in association with FIGS. 10-12. In addition, for a given length of first tube segment 101, this arrangement positions midpoint 102 of first tube segment 101 at a distance above guides 62 (illustrated as D1 in FIG. 5) selected for loading the arc-shaped midpoint 102 of first tube segment 101 just above a roller of rotor mechanism of a pump assembly, as further illustrated in association with FIGS. 10 and 12.

In some embodiments, the barbed outer surface 138 of end 134 of each respective connector 130 is replaced with a luer-type fitting or other fitting suitable for releasable mounting of tube segments 110,111 onto end 134 of the respective connectors 130 on opposite sides of the holder 45. This arrangement enables convenient replacement or exchange of tube segments 110,111 relative to holder 45 and relative to first tube segment 101.

In another embodiment, first tube segment 101 does not comprise a separate portion of tubing, but instead the three respective tube segments 101, 110, 111 form one single, continuous segment of tubing made of the same material. In this arrangement, connector 130 is not employed. However, as will be understood by those skilled in the art, other fasteners would be used to secure the first tube segment 101 of the continuous tubing relative to the respective guides 62 to maintain a fixed length and arcuate shape of first tube segment 101 between the respective guides 62, in accordance with principles of the present disclosure.

Figure 8:
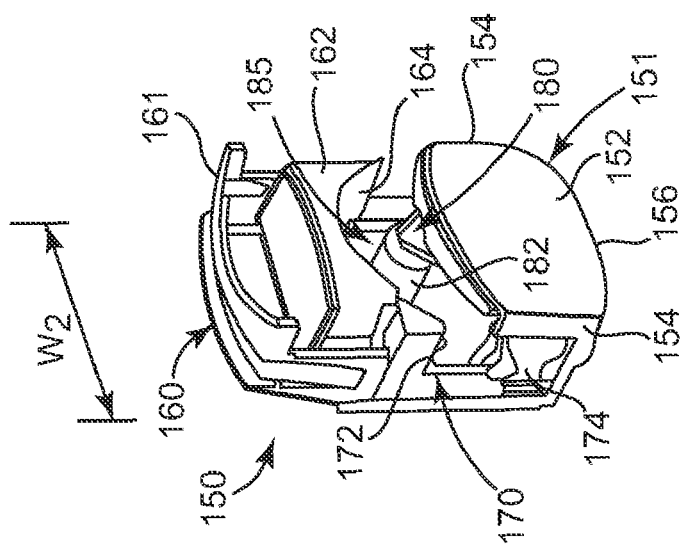
FIG. 8 is a perspective view of a pump assembly for use with the holder of FIGS. 1-6, in accordance with principles of the present disclosure.

Referring again to FIG. 1, the pump assemblies 14, 15 in which tubing array 100 is to be mounted (via holder 45) can take many forms. In some embodiments, the pump assemblies can take the form of a peristaltic pump assembly 150 shown in FIG. 8. As shown in FIG. 8, pump assembly 150 comprises a housing 151 that defines an exterior portion of pump assembly 150 and which includes a front body portion 152, a bottom portion 156, and a pair of opposite side portions 154. A cover mechanism 160 includes a pivotable door 161 and an engagement mechanism 162 that includes contact portion 164. The pump assembly 150 further comprises a rotor mechanism 180 (schematically illustrated in FIGS. 10, 12, and 14) that causes rotational movement of a plurality of rollers in a clock-wise movement (or counter clock-wise movement) in which each of the respective rollers pass in series by midportion 102 of the first tube segment 101 to push fluid through tubing array 100 in a controlled manner.

As illustrated in FIG. 8, one of the rollers (e.g., roller 182) is in an uppermost position within housing 151 of pump assembly 150. Together, the contact portion 164 of engagement mechanism 162 and the roller in the uppermost position (in this instance, roller 182) defines a roller-tube engagement zone 185.

In some embodiments, as further illustrated in FIG. 8, pump assembly 150 further comprises a tube-gripping mechanism 170 positioned on each side portion 154 of pump assembly 150 and located lateral to the roller-tube engagement zone 185. In general terms, the tube-gripping mechanism 170 acts to hold the ends 104 of the first tube segment 101 firmly in place during the slidable pressing action of a roller 182 (or subsequent roller) against midportion 102 of first tubing segment 101 through repeated cycles of peristaltic pumping. In some embodiments, the tube-gripping mechanism 170 comprises a generally stationary lower portion 174 and a slidably movable upper portion 172. In one aspect, when door 161 of cover mechanism 160 of pump assembly 150 is moved to a closed position, engagement mechanism 162 causes the upper portion 172 to slidably advance downward into a position closer to lower portion 174, thereby exerting a gripping force on ends 104 of first tubing segment 101. In this manner, the tube-gripping mechanism 170 acts to securely engage the ends 104 of first tubing segment 101 to maintain stable positioning of first tube segment 101 within roller-tube engagement zone 185 of pump assembly 150. This arrangement is further described and illustrated in association with FIG. 11.

As illustrated in FIGS. 5 and 8, a width W2 between the respective gripping mechanisms 170 of pump assembly 150 is slightly less than a width W1 between the laterally spaced apart guides 62. With this arrangement, upon slidably mounting holder 45 onto the exterior of housing 151 of pump assembly 150, the ends 104 of first tube segment 101 become properly aligned with and positioned for engagement by the upper portion 172 and lower portion 174 of gripping mechanism 170. In some embodiments, lower portion 174 of gripping mechanism 170 also acts as a protruding feature of housing 151 of pump assembly 150 to enable snap-fitting of holder 45, via its vertical ribs 59, onto the exterior of housing 151.

In one embodiment, pump assembly 150 comprises a positive displacement pump having substantially the same features as a Series 313 or 314 Peristaltic Pump available from Watson-Marlow Bredel Pumps Limited of Cornwall, United Kingdom.

Figure 9:
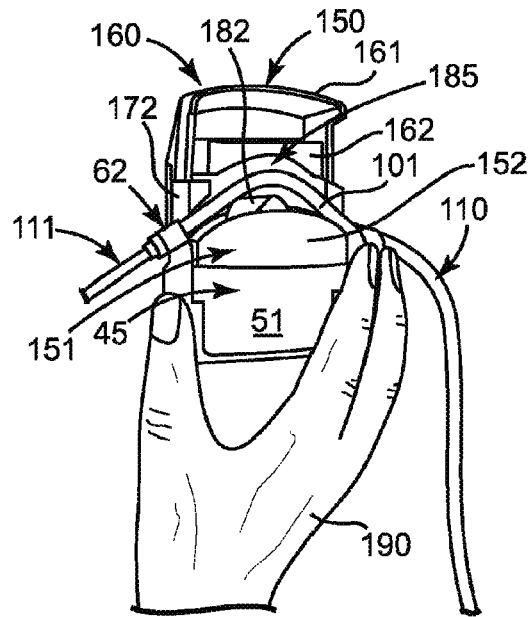
FIG. 9 is a perspective view illustrating a segment of tubing being loaded, via a holder, into a pump assembly, in accordance with principles of the present disclosure.
Figure 11:
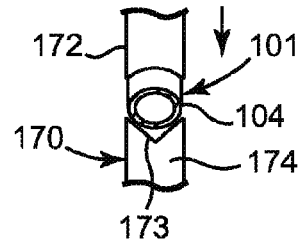
FIG. 11 is a side view of a portion of tubing as loaded into a tube-gripping mechanism of the pump assembly.

FIG. 9 is a schematic illustration of an operator using only one hand 190 to grasp holder 45 (in which tubing array 100 is mounted) and load first tubing segment 101 into pump assembly 150. In accordance with principles of the present disclosure, holder 45 defines a pocket-shaped shell that is sized and shaped to generally correspond to a size and shape of the housing 151 of pump assembly 150. Accordingly, by using a single hand, an operator can maneuver holder 45 into slidable engagement onto pump housing 151 which simultaneously and automatically loads the midportion 102 of first tube segment 101 within the roller-tube engagement zone 185. At the same time, as previously identified in association with FIGS. 5-8, by simply slidably fitting holder 45 onto pump housing 151, the configuration of the holder 45 also automatically aligns the ends 104 of first tube segment 101 within the respective tube-gripping mechanisms 170 located on opposite side portions 154 of the pump housing 151. Accordingly, holder 45 enables convenient and accurate loading of tubing array 101 within the pump assembly 150. Further details regarding this loading process is described and illustrated in association with FIGS. 10-15.

Figure 10:
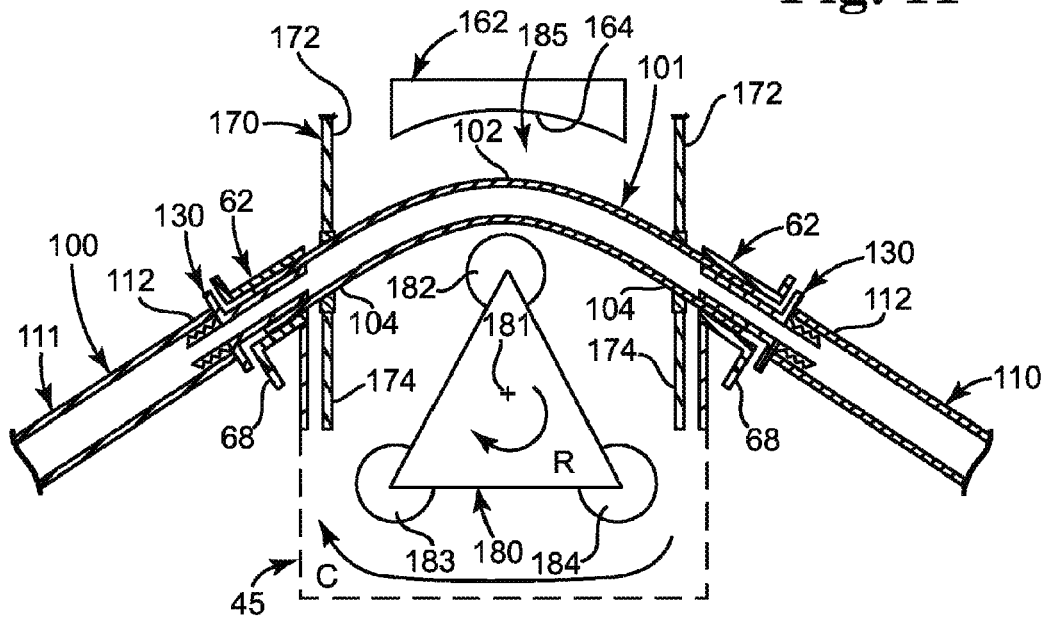
FIG. 10 is a cross-sectional view schematically illustrating a segment of tubing after being loaded via a holder into a pump assembly but prior to closure of the pump assembly, in accordance with principles of the present disclosure.

FIG. 10 is a cross-sectional view of FIG. 9 illustrating tubing array 100 as loaded relative to the pump assembly 150 prior to closing the door 161 of closing mechanism 160. As shown in FIG. 10, pump assembly 150 includes the rotor mechanism 180 configured to rotate (as indicated by directional arrow R) in a clock-wise direction to cause rollers 182, 183, and 184 to be moved in a circular pattern (as indicated by directional arrow C) about a center 181 of the rotor mechanism 180. In a manner well understood by those skilled in the art, with each cycle of rotation of rotor mechanism 180, each of the respective rollers 182, 183, 184 are moved sequentially into an uppermost position (currently occupied by roller 182) to extend within the roller-tube engagement zone 185 of the pump housing 151 for squeezing midportion 102 of first tube segment 101 against contact portion 164. However, as previously mentioned, in another aspect, rotor mechanism 180 is also configured to rotate in a counter clock-wise direction, causing rollers 182, 183, 184 to move in a direction opposite from that shown in FIG. 10.

Figure 12:
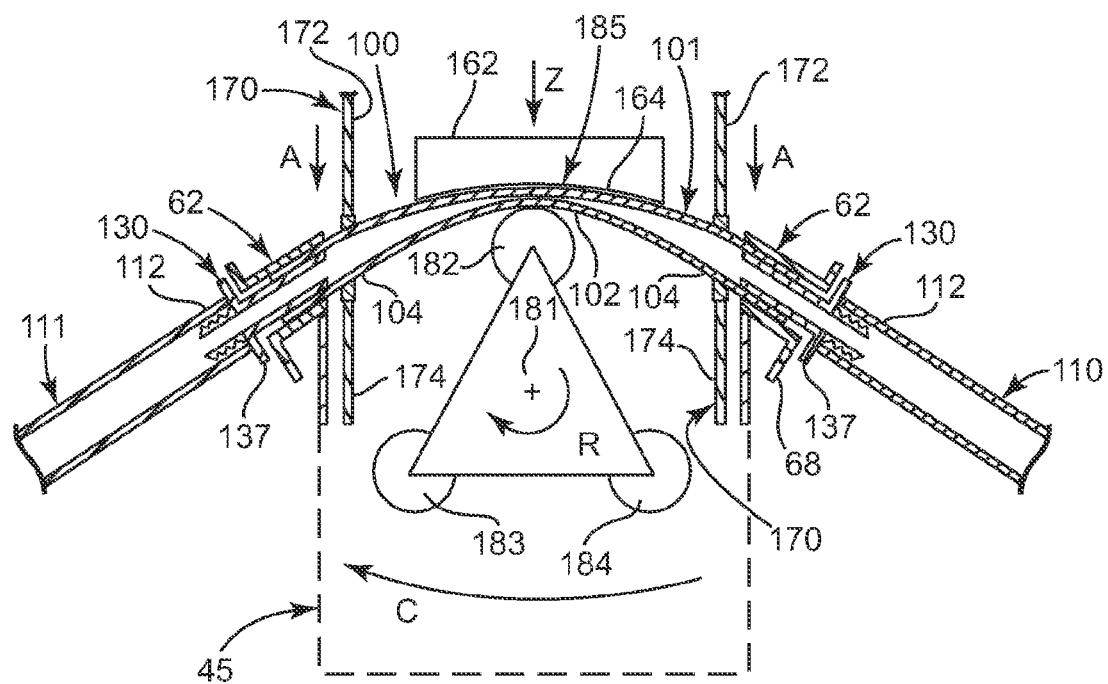
FIG. 12 is a cross-sectional view schematically illustrating the segment of tubing shown in FIG. 10 after closure of the pump assembly, in accordance with principles of the present disclosure.

In some embodiments, the array of rollers includes four rollers arranged at 90 degrees of spacing relative to each other instead of the three rollers 182, 183,184 arranged at the 120 degree spacing illustrated in FIGS. 10 and 12.

Accordingly, by using holder 45 in the one-handed technique described in association with FIG. 9, midportion 102 of first tube segment 101 is automatically loaded into the proper position just above the uppermost roller (roller 182 in this instance) and the ends 104 of first tube segment 101 become properly aligned within the respective gripping mechanisms 170 on each side of the pump assembly 150. In particular, as further illustrated in FIG. 11, the configuration of holder 45 causes each end 104 of the first tube segment 101 to be positioned within a V-shaped notch 173 of lower portion 174 of gripping mechanism 170. In particular, because the ends 104 of the first tube segment 101 are held by the guides 62 of holder 45 to remain in a generally singular plane in common with midpoint 102 of first tube segment 101 (as represented by line A in FIG. 6), placement of the holder 45 onto the housing 151 of pump assembly 150 to load midportion 102 of first tube segment 101 above the uppermost roller (roller 182 as shown in FIG. 10) necessarily results in the proper alignment of ends 104 of first tube segment 101 within the V-notch 173 of lower portion 174 of gripping mechanism 170.

Without such automatic positioning provided in accordance with principles of the present disclosure, manual installation of tubing according to conventional techniques frequently results in misalignment of tubing relative to the interior components of a pump assembly because of the many tasks to be accomplished simultaneously with both hands of an operator. Some of these tasks include manually positioning the tubing relative to one of the rollers of the pump, manually aligning the tubing within the side gripping mechanisms, and manually holding the positioned tubing while closing the door of the pump assembly.

With the proper loading of the tubing array 100 relative to the pump assembly 150 as shown in FIG. 10, the door 161 of the pump assembly 150 can be closed. As further illustrated in FIG. 12, closure of door 161 causes engagement member 162 to slidably advance downward (as represented by directional arrow Z) until contact portion 164 forcibly compresses midportion 102 of first tube segment 101 against the roller in the uppermost rotational position (in this instance, roller 182) within pump assembly 150. This action effectively closes the passageway within midportion 102 of first tube segment 101, and readies the pump assembly 150 for the rotation of the next roller (e.g., roller 183) into the uppermost position, upon initiation of a peristaltic pumping action via rotation of rotor mechanism 180.

In one aspect, the snap-fitting feature of holder 45 as provided via vertical ribs 59 (see, for example, FIGS. 2-3 and 5), maintains the front portion 51 of shell 50 in secure contact against the front portion 152 of housing 151 of pump assembly 150 during the closure of door 161 without having to hold the holder 45 in position against the pump assembly 150. Accordingly, after the convenient one-handed mounting of holder 45 onto pump assembly 150, the operator is free to let go of the holder 45 and then use the same hand to close the door 161 of the pump assembly 150. This positioning relationship maintained by the snap-fitting feature of holder 45, in turn, causes the ends 104 of first tube segment 101 to remain in proper alignment within the V-shaped lower portion 174 and within the upper portion 172 of tube-gripping mechanism 170 during closure of door 161. In addition, the close-fitting positioning relationship provided by the snap-fitting feature of holder 45 also causes midportion 102 of tube segment 101 to remain in position over the roller 182 in its uppermost position.

FIG. 12 also illustrates the gripping action of gripping mechanism 170 (as represented by directional arrow A) that secures the ends 104 of first tube segment between the upper portion 172 and the lower portion 174 of gripping mechanism 170 just inside the guides 62 of holder 45.

Figure 13:
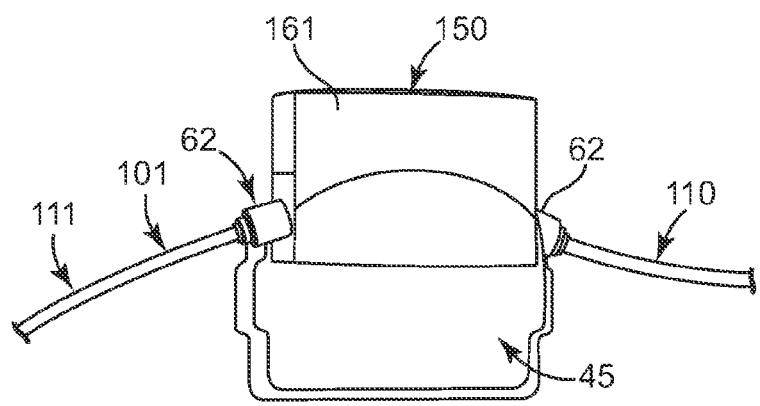
FIG. 13 is a perspective view schematically illustrating a holder slidably mounted onto a pump assembly with the segment of tubing properly loaded into the pump assembly of FIG. 10, in accordance with principles of the present disclosure.

FIG. 13 is a perspective view schematically illustrating tubing array 101 as loaded into pump assembly 150 with door 161 fully closed for operation of pump assembly 150. As illustrated in FIG. 13, guides 62 of holder 45 keep the respective second and third tube segments 110, 111 at the proper angle while maintaining the ends 104 of the first tube segment 101 at the proper angle within the pump assembly 150 to optimize engagement of midportion 102 of first tube segment 101 with one of the rollers 182, 183, 184 that is in the uppermost position within pump housing 151 (as previously illustrated in FIG. 12).

One of the factors contributing to optimum fluid flow produced by a peristaltic pump, such as pump assembly 150, includes placing one of the rollers of the pump into an uppermost position (or other consistent position) during loading of the tubing. However, at the same time, an operator must be careful when using their fingers to maneuver the rollers into the proper position prior to or during loading of the tubing. Accordingly, as described below in association with FIGS. 14-15B, a positioning system is provided to insure proper positioning of the rollers of the pump assembly during loading of the tubing, in accordance with principles of the present disclosure.

Figure 14:
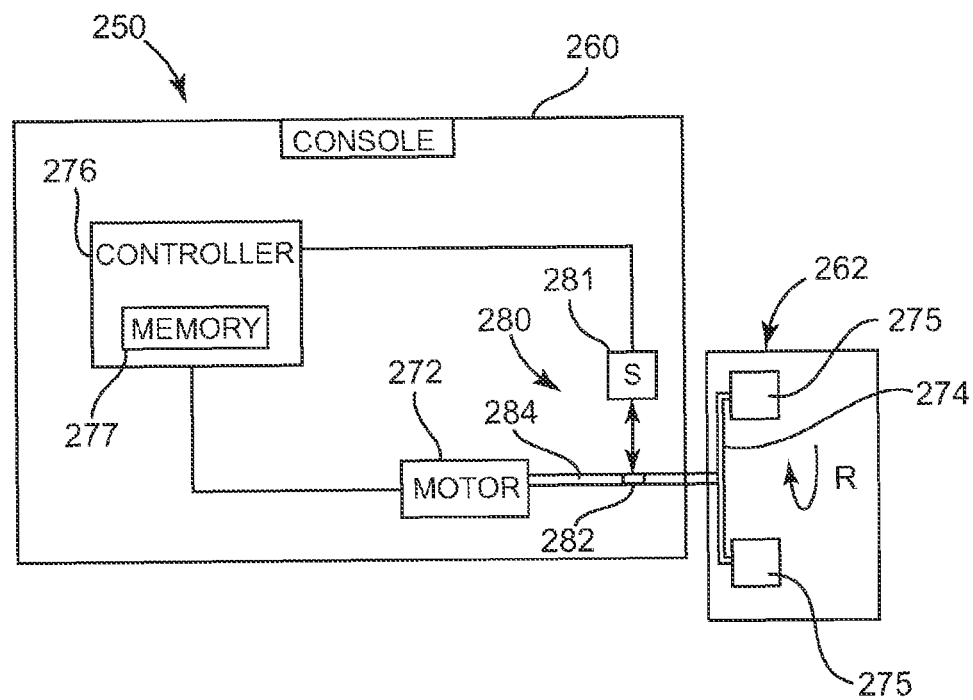
FIG. 14 is a block diagram schematically illustrating a mechanism for controlling a rotational position of a roller of the pump assembly, in accordance with principles of the present disclosure.

FIG. 14 is a block diagram schematically illustrating an optical sensing system 250, in accordance with principles of the present disclosure. As illustrated in FIG. 14, system 250 includes a fluid manager or console 260 configured to support a pump assembly 262, in a manner substantially similar to that depicted for console 12 and pump assemblies 14, 15 illustrated in FIG. 1. In general terms, console 260 enables mechanically mounting of a pump assembly 262 while also providing control circuitry to direct operations of the pump assembly 262. Accordingly, in some embodiments, console 260 comprises a controller 276 which controls operation of motor 272 for rotor mechanism 274 of pump assembly 262. The controller 276 employs algorithms stored in its memory 277 to initiate, suspend, and regulate the rotational movement of rotor mechanism 274 to cause a desired pumping action via engagement of rollers 275 with medical tubing.

In general terms, loading of tubing within pump assembly 262 in accordance with principles of the present disclosure includes using a positioning mechanism 280 to automatically position one of the rollers 275 into an uppermost position within the pump assembly 262 prior to and/or during loading of the tubing within the pump assembly 262. In some embodiments, positioning mechanism 280 includes a sensor 281 and an identifier 282 located on a shaft 284 driven by motor 272. In some embodiments, shaft 284 directly extends from motor 272 while in other embodiments, shaft 284 is coupled to a shaft directly extending from motor 272.

To load tubing within pump assembly 150, controller 276 activates motor 272 to move rotor mechanism 274 until one of the rollers 275 is in the uppermost position. To this end, identifier 282 is positioned on the shaft 284 so that alignment of identifier 282 with sensor 281 corresponds to one of the rollers 275 being in the uppermost position. In general terms, identifier 282 can take many forms resulting in the identifier 282 marking a unique rotational position of shaft 284. In one embodiment, identifier 282 comprises an optically detectable mark on shaft 284, as illustrated in FIG. 14.

In other embodiments, sensor 281 and identifier 282 are not limited to optical technologies but may comprise capacitive sensing, magnetic sensing, or other sensing technologies.

Figures 15A, 15B:
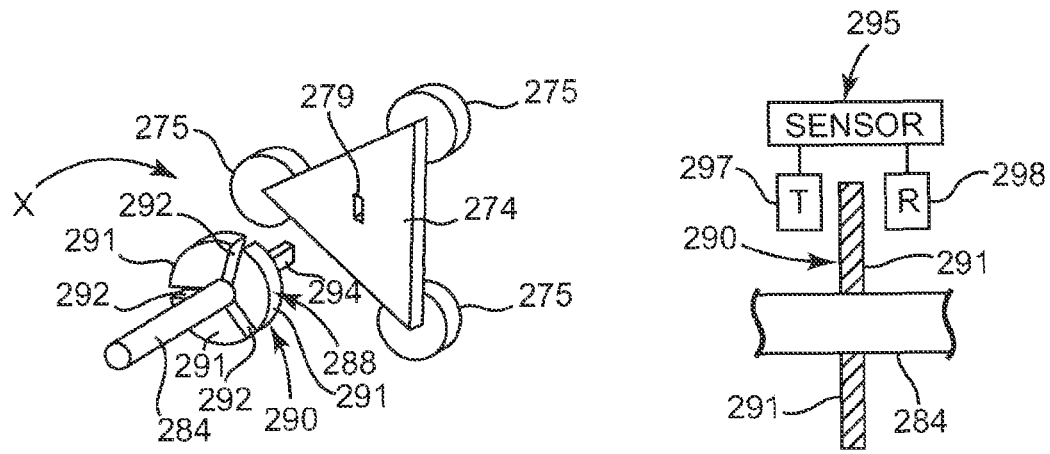
FIG. 15A is a perspective view schematically illustrating a mechanism for sensing a rotational position of a roller of the pump assembly, in accordance with principles of the present disclosure.
FIG. 15B is a perspective view schematically illustrating a sensor assembly for sensing a rotational position of a roller of the pump assembly, in accordance with principles of the present disclosure.

However, the identifier 282 and sensor 281 of the optically based positioning system 280 can take other forms, as illustrated in FIGS. 15A-15B. To this end, FIG. 15A illustrates a disc 290 mounted on shaft 284 with disc 290 defining a pattern of slits 292 formed between adjacent portions 291 of the disc 290. In this particular arrangement, the position of each slit 292 corresponds with a position of one of the respective rollers 275 (or one of rollers 182, 183, 184 in FIG. 12). In another aspect, disc 290 forms part of a mount assembly 288 coupled to shaft 284 and also defines a blade 294 protruding outward from disc 290. Blade 294 is configured to slidably engage slot 279 of rotor mechanism 274. In this manner, blade 294 of mount assembly 288 enables coupling rotor mechanism 274 to shaft 284 driven by motor 272 while patterned disc 290 enables sensing a position of the respective rollers.

As illustrated in FIG. 15B, a sensor assembly 295 is provided to optically detect the position of the slits 292 of disc 290. The sensor assembly 295 comprises a transmitter 297 and a receiver 298 which are arranged to straddle disc 290. As disc 290 rotates (as represented by directional arrow X in FIG. 15A), the sensor assembly 295 detects when one of the slits 292 passes between the transmitter 297 and receiver 298. Accordingly, by monitoring a position of the slits 292 of disc 290, controller 276 can maneuver the rollers 275 illustrated in FIG. 14 (or rollers 182, 183, 184 illustrated in FIG. 12) to insure that one of the respective rollers is in the uppermost position prior to loading tubing array 100 within a pump assembly.

Embodiments of the present disclosure provide a convenient, reliable, and reproducible means of properly positioning tubing within a peristaltic pump. Loading can be performed with one hand and with the knowledge that the full potential of the peristaltic pump will be employed to deliver fluid to the desired medical appliance.

Although the present disclosure has been described with reference to preferred embodiments, workers skilled in the art will recognize that changes can be made in form and detail without departing from the spirit and scope of the present disclosure.

What is claimed is:

1. A method of loading a peristaltic pump, the method comprising:

providing a holder with a pair of guides laterally spaced apart from each other and extending vertically upward from opposite side walls of the holder, wherein each respective guide of the pair of guides defines an elongate sleeve that forms an acute angle relative to a respective side wall of the holder to cause a longitudinal axis of the one elongate sleeve to be oriented toward a convergence with a longitudinal axis of the other elongate sleeve;

arranging a first tube segment to extend from one of the pair of guides to the other of the pair of guides and to be vertically spaced above a top edge of the holder;

slidably engaging the holder onto an exterior of a housing of the peristaltic pump to position a respective guide of the pair of guides externally on each of opposite sides of the housing to cause positioning of a midportion of the first tube segment within a housing of the peristaltic pump vertically above a first roller of the pump, wherein the first roller is an uppermost rotational position within the peristaltic pump, and wherein the convergence of the longitudinal axis of the respective sleeves is adjacent the first roller; and advancing a contact portion of the peristaltic pump toward the first roller to pressingly engage the midportion of the first tube segment between the contact portion and the first roller.

2. The method of claim 1, comprising:
arranging the pair of guides to extend in a plane common with the first tube segment so that upon slidably mounting of the holder onto the exterior of the housing of the pump and positioning of the midportion of the first tube segment above the first roller, a pair of outer ends of the first tube segment are positioned within a pair of tube-gripping mechanisms, wherein each respective tube-gripping mechanism is located at each of the opposite sides of the housing of the pump and each respective guide is positioned externally to, but in close proximity to, the respective tube-gripping mechanisms.

3. The method of claim 1, wherein slidably engaging the holder to position the midportion of the first tube segment comprises:
advancing the holder and the first tube segment in a first direction generally perpendicular to a plane in which the first tube segment extends in its loaded position.

4. The method of claim 2 wherein each tube-gripping mechanism comprises a concave, upper portion and a V-shaped, lower portion, and wherein advancing the contact portion of the pump further comprises manipulating a rotatable door into a closed position to force each respective concave, upper portion of the tube-gripping mechanism into pressing engagement against one of the respective ends of the first tube segment relative to one of the respective V-shaped, lower portions of the tube-gripping mechanism.

5. The method of claim 4 wherein slidably engaging the holder onto the exterior of the housing of the pump comprises:
snap-fitting the opposite side walls of the holder relative to the side portions of the housing of the peristaltic pump to maintain a front portion of the holder in secure contact against the housing of the peristaltic pump to thereby maintain the pair of outer ends of the first tube segment in proper alignment within the V-shaped, lower portions of the tube-gripping mechanism during advancement of the contact portion of the peristaltic pump toward the first roller and during pressing engagement of the midportion of the first tube segment.

6. The method of claim 2, wherein the guides are spaced apart and the first tube segment has a fixed length that is greater than a width of the holder between the pair of guides of the holder, and wherein the guides are spaced apart from each other by a distance substantially equal to a width of the housing of the peristaltic pump.

7. The method of claim 1, comprising:
using only one hand to grasp and hold the holder, without separately touching the first tube segment, during sliding insertion of the first tube segment into an interior of the peristaltic pump.

8. The method of claim 1, comprising:
using one of the pair of guides to releasably connect a second tube segment to a first end of the first tube segment to allow fluid communication therebetween; and
using the other of the pair of guides to releasably connect a third tube segment to a second end of the first tube segment to allow fluid communication therebetween,
wherein the second and third tube segments extend laterally outward in opposite directions from the first tube segment.

9. The method of claim 8 wherein the first tube segment is made of a first material different than a second material from which the second and third tube segments are made.

10. The method of claim 1, comprising:
arranging the peristaltic pump to include a peristaltic rotary mechanism configured to move an array of rollers that includes the first roller, in a circular pattern so that the array of rollers slidably engage the midportion of the first tube segment in series; and
automatically positioning the first roller into the uppermost rotational position prior to positioning the midportion of the first tube segment vertically above the first roller.

11. The method of claim 10, wherein automatically positioning the first roller comprises:
determining a position of the first roller relative to the uppermost rotational position via sensing a rotational position of an identifier coupled to a shaft supporting the peristaltic rotary mechanism.

12. A method of loading a peristaltic pump, the method comprising:
providing a holder with a pair of guides laterally spaced apart from each other and extending vertically upward from opposite side walls of the holder;
arranging a first tube segment to extend from one of the pair of guides to the other of the pair of guides and to be vertically spaced above a top edge of the holder;
slidably engaging the holder onto an exterior of a housing of the peristaltic pump to position a respective guide of the pair of guides externally on each of opposite sides of the housing to cause positioning of a midportion of the first tube segment within a housing of the peristaltic pump vertically above a first roller of the pump, wherein the first roller is an uppermost rotational position within the peristaltic pump; and
advancing a contact portion of the peristaltic pump toward the first roller to pressingly engage the midportion of the first tube segment between the contact portion and the first roller;
arranging the pair of guides to extend in a plane common with the first tube segment so that upon slidably mounting of the holder onto the exterior of the housing of the pump and positioning of the midportion of the first tube segment above the first roller, a pair of outer ends of the first tube segment are positioned within a pair of tube-gripping mechanisms, wherein each respective tube-gripping mechanism is located at each of the opposite sides of the housing of the pump and each respective guide is positioned externally to, but in close proximity to, the respective tube-gripping mechanisms,
wherein the first tube segment has a fixed length that is greater than a width of the holder between the pair of guides of the holder, and wherein the guides are spaced apart from each other by a distance substantially equal to a width of the housing of the peristaltic pump
wherein each respective guide of the pair of guides defines an elongate sleeve that forms an acute angle relative to a respective side wall of the to cause a longitudinal axis of the one elongate sleeve to be oriented toward a convergence with a longitudinal axis of the other elongate sleeve, wherein the convergence is adjacent to the first roller.

13. A tube-positioning system for loading tubing into a peristaltic pump, the system comprising
a holder including:
a shell sized and shaped to slidably fit onto an exterior of a housing of a peristaltic pump, wherein the shell includes a pair of opposite side walls laterally spaced apart from each other with each opposite side wall including a vertical rib configured to snap-fittingly engage a corresponding feature on a respective side of the exterior housing to releasably secure the shell relative to the exterior housing; and a pair of single guides protruding from an upper portion of the opposite side walls of the shell, wherein the pair of guides are laterally spaced apart by a distance substantially equal to a width of the exterior housing to cause the guides to be positioned laterally outward from an outer edge of the exterior housing; and a first tube segment extending between the pair of guides, the first tube segment including a pair of ends and a midportion, wherein the first tube segment has a fixed length so that the midportion forms an arcuate shape between the pair of guides upon each one of the pair of ends being removably secured within a respective guide of the pair of guides, wherein the one of the pair of guides is configured to removably receive a second tube segment to establish fluid communication between the second tube segment and the first tube segment, and wherein the other one of the pair of guides is configured to removably receive a third tube segment to establish fluid communication between the third tube segment and the first tube segment.

14. The tube-positioning system of claim 13 wherein the shell defines a pocket sized and shaped to correspond to a size and shape of the exterior housing and to at least partially enclose the exterior housing.

15. The tube-positioning system of claim 13, comprising:
a second tube segment removably secured by one of the pair of single guides into fluid communication with one of the outer ends of the first tube segment; and
a third tube segment removably secured by the other one of the pair of single guides into fluid communication with the other one of the outer ends of the first tube segment.

16. The tube-positioning system of claim 14, wherein the pocket includes a front portion and the opposite side walls of the shell define opposite side walls of the pocket with the opposite side walls extend generally perpendicular to the front portion, and wherein the opposite side walls are sized and shaped to extend generally parallel to an outer surface of the exterior housing.

17. A tube-positioning system for loading tubing into a peristaltic pump, the system comprising
a holder including:
a shell configured to slidably fit onto an exterior of a housing of a peristaltic pump, wherein the shell defines a pocket sized and shaped to correspond to a size and shape of the housing of the peristaltic pump, wherein the pocket securely engages the housing to hold the shell in a releasably fixed position relative to the housing of the peristaltic pump, and wherein the pocket includes a pair of opposite side portions laterally spaced apart from each other, wherein each of the opposite side portions includes a vertical rib configured to snap-fittingly engage a corresponding feature on a respective side of the housing of the peristaltic pump, and
a pair of single guides extending upward from the opposite side portions of the shell, wherein the pair of single guides are laterally spaced apart by a distance substantially equal to a width of the housing of the peristaltic pump;
a first tube segment extending between the single guides, the first tube segment including a pair of ends and a midportion, wherein the first tube segment has a fixed length so that the midportion forms an arcuate shape between the pair of single guides upon each one of the pair of ends being removably secured within a respective single guide of the pair of single guides;

a second tube segment removably secured by one of the pair of single guides into fluid communication with one of the outer ends of the first tube segment; and
a third tube segment removably secured by the other one of the pair of single guides into fluid communication with the other one of the outer ends of the first tube segment.

18. A tube-positioning system for loading tubing into a peristaltic pump, the system comprising
a holder including:
a shell configured to slidably fit onto an exterior of a housing of a peristaltic pump; and
a pair of guides extending upward from opposite side walls of the shell, wherein the pair of guides are laterally spaced apart by a distance substantially equal to a width of the housing of the peristaltic pump; and
a first tube segment extending between the pair of guides, the first tube segment including a pair of ends and a midportion, wherein the first tube segment has a fixed length so that the midportion forms an arcuate shape between the pair of guides upon each one of the pair of ends being removably secured within a respective guide of the pair of guides,
wherein the shell defines a pocket sized and shaped to correspond to a size and shape of the housing of the peristaltic pump, wherein the pocket securely engages the housing to hold the shell in a releasably fixed position relative to the housing of the peristaltic pump,
wherein each of the pair of guides defines an elongate sleeve that extends at an acute angle relative to a respective sidewall of the shell such that a longitudinal axis of one elongate sleeve converges with a longitudinal axis of the other elongate sleeve, wherein each elongate sleeve is sized and shaped to slidably receive a respective outer end of the first tube segment.

19. The tube-positioning system of claim 18, comprising:
a second tube segment removably secured by one of the pair of guides into fluid communication with one of the outer ends of the first segment; and
a third tube segment removably secured by the other one of the pair of guides into fluid communication with the other one of the outer ends of the first tube segment.

20. The tube-positioning system of claim 19, further comprising a fluid delivery system comprising:
a pump body including:
a contact portion;
a rotor mechanism for rotatably moving an array of rollers that includes a first roller, in a circular path so that when the first roller is in an uppermost position, the midportion of the first tube segment is positioned within a roller tube engagement zone defined by the contact portion and the first roller,
wherein the acute angle of the elongate sleeves and the fixed length of the first tube segment are selected to orient the midportion of the first tube segment to extend within the roller-tube engagement zone.

21. The tube-positioning system of claim 20, further comprising:
a console configured to removably receive the housing of the pump into a mounted position and including a rotor positioning system that comprises:
a controller;
a motor including a shaft coupled to the rotor mechanism to cause rotation of the rotor mechanism;
an identifier coupled to the shaft; and
a sensor in electrical communication with the controller and aligned to detect the identifier, wherein the controller is configured to cause rotation of the shaft, prior to loading of the first tube segment into roller-tube engagement zone of the pump, to position the rotor mechanism until the first roller is located in the uppermost position within the pump body as indicated by the position of the identifier relative to the sensor.

22. A fluid delivery system comprising:
means for using a one-handed application to automatically load a first tube segment within a roller-tube engagement zone of a peristaltic pump while holding opposite ends of the first tube segment at a position external to, and at opposite sides of, an exterior of the peristaltic pump so that the first tube segment maintains a fixed length and forms an arcuate shape during loading within the roller-tube engagement zone; and
means for automatically positioning a first roller of an array of rollers at the roller-tube engagement zone of the peristaltic pump prior to loading the first tube segment, wherein the means for automatically loading comprises:
a shell configured to slidably fit onto the exterior of the pump, wherein the shell
defines a pocket sized and shaped to correspond to a size and shape of the exterior of the peristaltic pump, wherein the pocket securely engages the exterior of the peristaltic pump to hold the shell in a releasably fixed position relative to the exterior of the peristaltic pump, the shell including a pair of guides extending upward from opposite side walls of the shell, wherein each guide defines an elongate sleeve extending at an acute angle relative to a respective side wall of the shell; and
the first tube segment extending between the pair of guides of the shell, the
first tube segment including the opposite ends and a midportion, wherein the first tube segment has a fixed length so that the midportion forms the arcuate shape upon each of the opposite ends being removably secured within a respective elongate sleeve of a respective guide of the pair of guides.

23. The fluid delivery system of claim 22 wherein the means for automatically positioning comprises:
the roller-tube engagement zone including a contact portion and a rotor mechanism for rotatably moving the array of rollers in a circular path so that when the first roller is in an uppermost position, the midportion of the first tube segment is aligned to be pressingly engaged between contact portion and the first roller,
wherein the acute angle of the elongate sleeves and the fixed length of the first tube segment are selected to orient the midportion of the first tube segment to extend between the first roller and the contact portion; and
a console configured to removably receive the peristaltic pump in a mounted position and including a rotor positioning system that comprises:

a controller;
a motor coupled via a shaft to the rotor mechanism to cause rotation of the rotor mechanism;
an identifier coupled to the shaft; and
a sensor in electrical communication with the controller and aligned to detect the identifier,
wherein the controller is configured to cause rotation of the shaft, prior to loading of the first tube segment into the roller tube engagement zone, to position the rotor mechanism until the first roller is located in the uppermost position within the peristaltic pump as indicated by a detection of a position of the identifier by the sensor.

24. A fluid delivery system, comprising:
a peristaltic pump including a roller-tube engagement zone including a contact portion and a rotor mechanism for rotatably moving an array of rollers, that includes a first roller, in a circular path;
a console configured to removably receive the peristaltic pump in a mounted position, the console including a rotor positioning system that comprises:
a controller;
a motor coupled via a shaft to the rotor mechanism to cause rotation of the rotor mechanism;
an identifier coupled to the shaft; and
a sensor in electrical communication with the controller and aligned to detect the identifier,
wherein the controller is configured to cause rotation of the shaft, prior to loading of the tubing into the roller-tube engagement zone, to position the rotor mechanism until the first roller is located in the uppermost position within the peristaltic pump as indicated by a detection of a position of the identifier by the sensor; and
a holder including:
a shell configured to slidably fit onto an exterior of a housing of the peristaltic pump, the shell defining a pocket sized and shaped to correspond to a size and shape of a housing of the peristaltic pump, wherein the pocket securely engages the housing to hold the shell in a releasably fixed position relative to the housing of the peristaltic pump, and wherein the shell defines a pair of opposite sidewalls; and
a pair of guides extending upward from the opposite side walls of the shell, wherein each of the pair of guides defines an elongate sleeve that extends at an acute angle relative to a respective sidewall of the shell such that a longitudinal axis of one elongate sleeve converges with a longitudinal axis of the other elongate sleeve, wherein each elongate sleeve is sized and shaped to slidably receive one end of opposite ends of a tube segment to cause the tube segment to extend between the respective guides.

* * * * *

UNITED STATES PATENT AND TRADEMARK OFFICE
CERTIFICATE OF CORRECTION

| | |
|---|---|
| PATENT NO. | : 8,272,857 B2 |
| APPLICATION NO. | : 12/036148 |
| DATED | : September 25, 2012 |
| INVENTOR(S) | : Gerould W. Norman et al. |

Page 1 of 1

It is certified that error appears in the above-identified patent and that said Letters Patent is hereby corrected as shown below:

Column 13, line 1, delete "single"

Signed and Sealed this
Nineteenth Day of February, 2013

Teresa Stanek Rea
*Acting Director of the United States Patent and Trademark Office*